(12) United States Patent
Griffiths et al.

(10) Patent No.: US 6,469,015 B1
(45) Date of Patent: Oct. 22, 2002

(54) PHARMACEUTICAL FORMULATION

(75) Inventors: Hazel-Ann Griffiths, Dorking; Alan John Goodall; Joshua Oduro-Yeboah, both of Worthing, all of (GB)

(73) Assignee: Novartis International Pharmaceutical Ltd, Hamilton (BM)

( * ) Notice: Subject to any disclaimer, the term of this patent is extended or adjusted under 35 U.S.C. 154(b) by 0 days.

(21) Appl. No.: 08/462,257

(22) Filed: Jun. 5, 1995

Related U.S. Application Data

(63) Continuation of application No. 08/378,107, filed on Jan. 25, 1995, now abandoned, which is a continuation of application No. 08/217,463, filed on Mar. 24, 1994, now abandoned, which is a continuation-in-part of application No. 07/910,114, filed as application No. PCT/GB91/00102 on Jan. 24, 1991, now abandoned.

(51) Int. Cl.$^7$ ............................................... A61K 31/52
(52) U.S. Cl. ....................................... 514/262; 514/264
(58) Field of Search .................................. 514/262, 264

(56) References Cited

U.S. PATENT DOCUMENTS

| | | | |
|---|---|---|---|
| 4,845,084 A | 7/1989 | Hannah et al. | ................ 514/81 |
| 4,942,166 A | 7/1990 | Harnden et al. | ............ 514/262 |

FOREIGN PATENT DOCUMENTS

| | | | |
|---|---|---|---|
| EP | 0 042 827 | 6/1981 | ............ A61K/9/10 |
| EP | 0 044 543 | 1/1982 | ............ A61K/9/10 |
| EP | 0 095 813 | 12/1983 | .......... A61K/31/52 |
| EP | 0 141 927 | 5/1985 | ......... C07D/473/18 |
| EP | 0 152 316 | 8/1985 | ......... C07D/473/32 |
| EP | 0216459 | * 1/1987 | .......... A61K/31/52 |
| EP | 0 216 459 | 4/1987 | ......... C07D/473/18 |
| EP | 0 416 739 | * 3/1991 | .......... A61K/31/52 |

OTHER PUBLICATIONS

German et al, Chemical Abstracts, 115, 35756w (1991)(non-certified English Translation).
Cooper et al., J. Pharm. Sci., vol. 74, No. 6, 1985, pp. 688–689.
Baker 71 CA: 42259n, 1969.*
Griffiths etal 115 CA:35756w 1991.*
Griffiths etal 115 CA:142339j 1991.*
Remingtons' Pharmaceutical Sciences 17$^{th}$ Ed 1985 P 1305.*
Hodge etal, 1989, Antimicro Agent & Chemotherapy 33(2) P 223–29.*

* cited by examiner

*Primary Examiner*—Russell Travers
(74) *Attorney, Agent, or Firm*—Thomas R. Savitsky

(57) ABSTRACT

An oil-in-water topical pharmaceutical formulation or an aqueous formulation for the treatment of virus infections of the skin or mucosa, comprising at least 30% of propylene glycol and solubilized penciclovir.

29 Claims, No Drawings

PHARMACEUTICAL FORMULATION

This application is a continuation of Ser. No. 08/378,107 filed Jan. 25, 1995, abandoned, which is a continuation of U.S. Ser. No. 08/217,463, filed Mar. 24, 1994, abandoned, which is a continuation-in-part application of U.S. Ser. No. 07/910,114, filed Feb. 17, 1993, abandoned, which is the §371 national stage entry of PCT/GB91/00102, filed Jan. 24, 1991.

This invention relates to a topical pharmaceutical formulation suitable for use in the treatment of virus infections of the skin and mucosa.

EP-A-141927 (Beecham Group p.l.c.) discloses the compound 9-(4-hydroxy-3-hydroxymethylbut-1-yl)guanine, known as BRL 39123 or penciclovir, its salts and esters thereof and its use in the treatment of herpesvirus infections. Topical administration is disclosed as a suitable route. Hereinafter, references to penciclovir include salts and esters thereof.

It is important with a topical formulation of an antiherpesvirus drug that the quantity of drug released from the formulation is sufficient to exert a significant antiviral effect and that the drug rapidly reaches its site of action within the skin.

Rapid penetration is important, since in most cases, major virus induced epidermal pathology occurs within the first 24 hours post infection. Once the infection is established and the stratum corneum has been eroded, the rapid ingress of host resistant factors could make chemotherapy of questionable value.

A new antiviral topical formulation has now been discovered, having improved properties as compared with conventional formulations.

Accordingly, the present invention provides an oil-in-water topical pharmaceutical formulation or an aqueous formulation for the treatment of virus infections of the skin or mucosa, comprising at least 30% of propylene glycol and solubilised penciclovir.

Such a topical formulation may contain 0.075% to 10% w/w penciclovir and from 30% to 60% w/w of propylene glycol and from 15% w/w water (up to 50% when there is an oil phase).

In a preferred aspect the formulation comprises from 0.75 or 1% to 10% w/w penciclovir, from 30% to 50% w/w of propylene glycol, from 20% w/w water (up to 40%, when there is an oil phase). Examples of suitable formulations comprise from 2% to 5% w/w penciclovir, from 35% to 45% w/w of propylene glycol, from 25% to 40% w/w water together with an oil phase. A preferred formulation comprises 0.75% or 1% to 5% penciclovir. The formulation should preferably contain about 40% w/w of propylene glycol.

The amount of penciclovir present in the formulation should be at least sufficient to maintain an antivirally effective concentration at the site of infection between applications without showing signs of toxicity. The optimum concentration of penciclovir will depend on its solubility in the vehicle. Penciclovir may be included in the formulation at a level exceeding its solubility in order to provide a reservoir and to maintain the antiviral agent at a saturated concentration within the vehicle. One suitable amount in the above preferred formulation is 0.5–10% w/w, such as 2–8%, for example 5%. A preferred amount is less than 5%, such as 0.5 to 2%, for example 1%.

EP-A-416739 (Beecham Group p.l.c.) discloses a topical formulation comprising at least 30% propylene glycol, 0.1 to 10.0% decylmethylsulphoxide and solubilised penciclovir. It will be appreciated that the present formulation comprises less than 0.1% decylmethylsulphoxide.

The water used in the formulation is preferably purified water, purified that is by distillation by means of ion exchange or other appropriate method.

The oil phase of the emulsions of this invention may be constituted from known ingredients in a known manner. While the phase may comprise merely an emulsifier (otherwise known as an emulgent), it is desirably comprised of a mixture of at least one emulsifier with one or more excipients including oils, fats and/or waxes, together with optional film formers and stabilisers as well as thickening and bodying agents. Preferably, as explained in more detail below, an additional hydrophilic emulsifier is included together with a lipophilic emulsifier which acts as a stabiliser. It is also preferred to include both an oil and a fat. Together, the emulsifier(s) make up the so-called emulsifying wax, and the wax together with the oil and/or fat make up the so called emulsifying ointment base which forms the oil dispersed phase of the emulsions.

Oil-in-water topical formulations may be formulated in a number of ways, all of which depend primarily on the alignment of the emulgent or emulsifying agent and emulsion stabiliser at the oil/water interface, with the non-polar or lipophilic groups soluble in the oil phase and the polar or hydrophilic groups in the aqueous or continuous phase. Thus the more polar hydrophilic emulgents result in oil-in-water emulsions. This principle has been systemised in the idea of a 'hydrophilic-lipophilic balance' (H.L.B.) Griffen, W. C. *J. Soc. Cosmet. Chem.*, 1954, 5, 249 and the various emulgents have been allocated H.L.B. numbers from which their behaviour with constituents of the aqueous and oil phases (to which are applied theoretical required H.L.B. figures) may be predicted.

Emulgents and emulsion stabilisers suitable for use in the formulation of the present invention include polyoxyethylene sorbitan monostearate (polysorbate 60), sorbitan monostearate, sorbitan monooleate, cetostearyl alcohol, myristyl alcohol, glyceryl monostearate, sodium lauryl sulphate, Cetomacrogol 1000 and Carbomer 940.

A preferred stabiliser is Cetomacrogol 1000 (Polyethylene Glycol 1000 Monocetyl Ether) and is preferably present in a percentage of 0.5 to 2% of the composition, such as 0.5 to 1%, for example 0.7 to 1.0%, preferably 0.9% to 1.0%, the optimum concentrations being 0.94%.

The choice of suitable oils or fats for the formulation is based on achieving the desired cosmetic properties. Thus the cream should preferably be non-greasy, non-staining and washable product with suitable consistency to avoid leakage from tubes or other containers. Lipophilic substances with relatively high melting points, such as beeswax, partial glycerides of capric and caprylic acids, or silicone oil, white soft paraffin and/or liquid paraffin or other mineral or vegetable oils are suitable. Straight or branched chain, mono- or dibasic alkyl esters such as di-isopropyladipate, isocetyl stearate, propylene glycol diester of coconut fatty acids, isopropyl myristate, decyl oleate, isopropyl palmitate, butyl stearate, 2-ethylhexyl palmitate or a mixed ester of 2-ethyl hexanoic acid with a blend of cetyl or stearyl alcohols known as Crodamol CAP may also be used.

As well as creams, the aqueous/oil-in-water formulation may be a lotion, skin paint, gel, spray, aerosol, liniment or gel stick, which are formulated as known in the art, for example as described in standard text books of pharmaceutics and cosmetics, such as Harry's Cosmeticology published by Leonard Hill Books, the British Pharmacopoeia, USP twenty-first revision (USP XXI) (1984), distributed by Mack Publishing Company.

The product may or may not be sterile, with adequate preservative capacity for single or multi-dose purposes.

In this description, the following terms are employed:

Aerosol-Pharmaceutical aerosols are products that are packaged under pressure and contain therapeutically active ingredients that are released upon activation of an appropriate valve system The term 'aerosol' has been used to refer to the fine mist of spray that is emitted from a pressurized container containing an active ingredient and a propellant. However, the term has been broadly applied to include all self-contained pressurized products, some of which deliver foams or semisolid fluids. Accordingly, unless indicated otherwise, a reference herein to an aerosol formulation of the present invention should be understood to include pharmaceutical compositions for topical use comprising a pharmaceutically acceptable carrier which includes a propellant, said compositions being adapted for use in a pressurized container that dispenses the composition as a spray, foam or semisolid liquid.

An aerosol generally comprises a container, a propellant, a concentrate containing the active ingredient, a valve (which may be a metered valve), and an actuator. The nature of these components determines characteristics such as delivery rate, foam density, and fluid viscosity Aerosols may be two-phase (gas and liquid) or three-phase (gas, liquid, and solid or liquid formulations. A two-phase formulation consists of a solution of active ingredients in liquidified propellant and the vaporized propellant. The solvent may be the propellant or a mixture of the propellant and co-solvents such as alcohol and polyethylene glycols which are often used to enhance the solubility of the active ingredients. Three-phase formulations consist of a suspension or emulsion of the active ingredients) in addition to the vaporized propellants. A suspension consists of the active ingredient(s) dispersed in the propellant system with the aid of suitable excipients such as wetting agents and/or solid carriers such as talc or colloidal silicas. A foam formulation is generally an emulsion containing one or more active ingredients, surfactants, aqueous or nonaqueous liquids, and the propellants. If the propellant is in the internal (discontinuous) phase (i.e., of the oil-in-water type), a stable foam is discharged, and if the propellant is in the external (continuous) phase (i.e., of the water-in-oil type), a spray or a quick-breaking foam is discharged. [See *The United States Pharmacopeia, XXI* ('USP') at 1334].

Gels—Gels are semisolid systems consisting either of suspensions made up of small inorganic particles or of large organic molecules interpenetrated by a liquid. Where the gel consists of a network of small discrete particles, the gel is classified as a two phase system. In a two-phase gel, if the particle size of the dispersed phase is relatively large, the gel is sometimes referred to as a magma. Both gels and magmas may be thixotropic, forming semisolids on standing and becoming liquid on agitation.

Single-phase gels consist of organic macromolecules uniformly distributed throughout a liquid so that no apparent boundaries exist between the dispersed macromolecules and the liquid. Single-phase gels may be made from synthetic macromolecules (e.g. Carbomer)* or from natural gums (e.g. Tragacanth). The latter preparations are also called mucilages. Although single-phase gels are commonly aqueous, alcohols and oils may also be used as the continuous phase. For example, mineral oil can be combined with a polyethylene resin to form a gel which may be used as an oleaginous ointment base [see *USP,* supra at 1336].

*Excipients that are underlined in this discussion are classified as pharmacopoeial preparations (USP or BP).

Lotion—Preferred lotions include fluid or thixotropic emulsions intended for external application to the body. These lotions are emulsions of the oil-in-water type stabilized by a surface-active agent. They may separate or stratify on long standing, and should be well shaken before each use. Adequate preservation against microbial contamination is required [see *USP,* supra at 1337].

Gel stick—The definition of gel sticks set forth in *Harry's Cosmeticology,* 6th Edition, at 740, is hereby incorporated herein by reference.

Liniment—Liniments are solutions or mixtures of various substances in oil, alcoholic solutions of soap, or emulsions, as in the present invention. They are intended for external application and are usually applied with friction and rubbing of skin, the oil or soap base providing for ease of application and massage.

Spray—As used in this description, spray formulations are aqueous solutions of various drugs which are applied topically from a container having a spray means (eg., an atomizer or nebulizer).

The present invention further provides a method for the preparation of a topical pharmaceutical formulation, as hereinbefore defined, which comprises mixing the combination of penciclovir, propylene glycol and water, optionally with oil phase.

The manner of formulating an emulsion will of course vary according to the amount and nature of the constituents, but nevertheless follows known techniques in emulsion technology (see The Pharmaceutical Codex, London, The Pharmaceutical Press, 1979). In a preferred method penciclovir may be included in the oil phase prior to emulsification with the aqueous portion. Alternatively the penciclovir may be initially incorporated wholly in the aqueous portion where it may form a solution alone, or mixed solution/suspension, and then emulsified with the ointment base, or a part of the aqueous portion may be formulated as an emulsion, and the balance of the water, propylene glycol and penciclovir added to and dispersed into the emulsion. In using these procedures, it is preferable to heat the aqueous portion and the oil phase to about 40 to 80° C., preferably 50 to 70° C., prior to emulsification which may be achieved by vigorous agitation using for example a standard laboratory mixer. Finer dispersions of the oil phase may be obtained by homogenising or milling in a colloidal mill.

A topical formulation of the present invention may be used in the treatment or prevention of viral infections caused by herpesviruses such as herpes simplex types 1 and 2 and varicella-zoster virus.

The formulation should be applied in the infected area 2 to 6 times daily, preferably 2 or 3 times.

The following examples illustrate the invention.

Creams Containing Propylene Glycol

EXAMPLE 1

| Oil phase | |
|---|---|
| Polawax NF | 18.0 |
| White soft paraffin | 10.0 |
| BRL 39123 (penciclovir) | 5.0 |
| Aqueous phase | |
| Sodium lauryl sulphate | 0.75 |
| Propylene glycol | 40.0 |
| Purified Water to | 100.0 |

EXAMPLE 2

| Oil phase | |
|---|---|
| Cetostearyl alcohol | 6.72 |
| White soft paraffin | 13.78 |
| Glyceryl monostearate | 7.50 |
| BRL 39123 (penciclovir) | 2.0 |
| Aqueous phase | |
| Sodium lauryl sulphate | 0.75 |
| Propylene glycol | 40.0 |
| Purified water to | 100.0 |

EXAMPLE 3

| Oil phase | |
|---|---|
| Cetostearyl alcohol | 7.41 |
| White soft paraffin | 14.25 |
| Liquid paraffin | 5.70 |
| BRL 39123 (penciclovir) | 3.0 |
| Aqueous phase | |
| Sodium lauryl sulphate | 0.86 |
| Propylene glycol | 40.0 |
| Purified water to | 100.0 |

EXAMPLE 4

| Oil phase | |
|---|---|
| Cetostearyl alcohol | 7.8 |
| White soft paraffin | 15.0 |
| Light mineral oil | 6.0 |
| BRL 39123 (penciclovir) | 0.5 |
| Aqueous phase | |
| Cetomacrogol 1000 | 0.9 |
| Propylene glycol | 40.0 |
| Purified water to | 100.0 |

EXAMPLE 5

| Oil phase | |
|---|---|
| Cetostearyl alcohol | 7.8 |
| White soft paraffin | 15.0 |
| Dibutyladipate | 20.0 |
| BRL 39123 (penciclovir) | 0.5 |
| Aqueous phase | |
| Sodium lauryl sulphate | 0.9 |
| Propylene glycol | 25.0 |
| Purified water to | 100.0 |

EXAMPLE 6

| Aqueous phase | |
|---|---|
| Sodium lauryl sulphate | 0.85 |
| Propylene glycol | 40.00 |
| Purified water | 26.07 |
| Oil phase | |
| Cetostearyl alcohol | 7.33 |
| Liquid paraffin | 5.64 |
| Carbomer 940 | 1.00 |
| BRL 39123 (penciclovir) | 5.00 |
| White soft paraffin to | 100.00 |

EXAMPLE 7

| Oil phase | |
|---|---|
| Cetostearyl alcohol | 7.80 |
| Liquid paraffin | 6.00 |
| White soft paraffin | 15.00 |
| BRL 39123 (penciclovir) | 5.00 |
| Aqueous phase | |
| Cetomacrogol 1000 | 0.90 |
| Propylene glycol | 40.00 |
| Purified water to | 100.00 |

EXAMPLE 8

| Oil phase | |
|---|---|
| Cetostearyl alcohol | 7.41 |
| Liquid paraffin | 5.70 |
| White soft paraffin | 14.25 |
| BRL 39123 (penciclovir) | 5.00 |
| Aqueous phase | |
| Cetomacrogol 1000 | 0.85 |
| Propylene glycol | 40.00 |
| Purified water to | 100.00 |

EXAMPLE 9

| Aqueous phase | |
|---|---|
| Cetomacrogol 1000 | 0.94 |
| Propylene glycol | 41.79 |
| Purified water | 27.94 |
| Oil phase | |
| Cetostearyl alcohol | 7.74 |
| Liquid paraffin | 5.96 |
| BRL 39123 (penciclovir) | 0.75 |
| White soft paraffin to | 100.00 |

EXAMPLE 10

| Aqueous phase | |
|---|---|
| Cetomacrogol 1000 | 0.94 |
| Propylene glycol | 41.68 |
| Purified water | 27.87 |
| Oil phase | |
| Cetostearyl alcohol | 7.72 |
| Liquid paraffin | 5.94 |
| BRL 39123 (penciclovir) | 1.00 |
| White soft paraffin to | 100.00 |

EXAMPLE 11

| Aqueous phase | |
|---|---|
| Cetomacrogol 1000 | 0.93 |
| Propylene glycol | 41.26 |
| Purified water | 27.58 |
| Oil phase | |
| Cetostearyl alcohol | 7.64 |
| Liquid paraffin | 5.88 |
| BRL 39123 (penciclovir) | 2.00 |
| White soft paraffin to | 100.00 |

EXAMPLE 12

| Aqueous phase | |
|---|---|
| Cetomacrogol 1000 | 0.90 |
| Propylene glycol | 40.00 |
| Purified water | 26.74 |
| | % w/w |
| Oil phase | |
| Cetostearyl alcohol | 7.41 |
| Liquid paraffin | 5.70 |
| BRL 39123 (penciclovir) | 5.00 |
| White soft paraffin to | 100.00 |

EXAMPLE 13

| Oil phase | |
|---|---|
| Cetostearyl alcohol | 7.41 |
| Liquid paraffin | 5.70 |
| White soft paraffin | 14.25 |
| BRL 39123 (penciclovir) | 5.00 |
| Aqueous phase | |
| Cetomacrogol 1000 | 1.80 |
| Propylene glycol | 40.00 |
| Purified water to | 100.00 |

EXAMPLE 14

| Oil phase | |
|---|---|
| Cetostearyl alcohol | 7.41 |
| White soft paraffin | 14.25 |
| Liquid paraffin | 5.70 |
| BRL 39123 (penciclovir) | 5.00 |
| Aqueous phase | |
| Cetomacrogol 1000 | 1.14 |
| Propylene glycol | 40.00 |
| Purified water to | 100.00 |

EXAMPLE 15

| Oil phase | |
|---|---|
| Cetostearyl alcohol | 7.41 |
| White soft paraffin | 14.25 |
| Liquid paraffin | 0.70 |
| Ethyl Oleate | 5.00 |
| BRL 39123 (penciclovir) | 5.00 |
| Aqueous phase | |
| Cetomacrogol 1000 | 1.14 |
| Propylene Glycol | 40.00 |
| Purified water to | 100.00 |

EXAMPLE 16

| Oil phase | |
|---|---|
| Cetostearyl alcohol | 7.41 |
| White soft paraffin | 14.25 |
| Liquid paraffin | 0.70 |
| Oleic acid | 5.00 |
| BRL 39123 (penciclovir) | 5.00 |
| Aqueous phase | |
| Cetomacrogol 1000 | 1.14 |
| Propylene Glycol | 40.00 |
| Purified water to | 100.00 |

EXAMPLE 17

| Oil phase | |
|---|---|
| Cetostearyl alcohol | 7.41 |
| White soft paraffin | 14.25 |
| Liquid paraffin | 0.70 |
| Glyceryl linoleate | 5.00 |
| BRL 39123 (penciclovir) | 5.00 |
| Aqueous phase | |
| Cetomacrogol 100 | 1.14 |
| Propylene glycol | 40.00 |
| Purified water to | 100.00 |

EXAMPLE 18

| Oil phase | |
|---|---|
| Cetostearyl alcohol | 7.41 |
| White soft paraffin | 9.95 |
| IMWITOR 312* | 10.00 |
| BRL 39123 (penciclovir) | 5.00 |
| Aqueous phase | |
| Cetomacrogol 1000 | 1.14 |
| Propylene Glycol | 40.00 |
| Purified water to | 100.00 |

EXAMPLE 19

| Oil phase | |
|---|---|
| Cetostearyl alcohol | 7.41 |
| IMWITOR 312* | 20.00 |
| BRL 39123 (penciclovir) | 5.00 |
| Aqueous phase | |
| Cetomacrogol 1000 | 1.14 |
| Propylene glycol | 40.00 |
| Purified water to | 100.00 |

METHOD OF MANUFACTURE

Components of the oil phase were heated to 65–70° C., with constant stirring, until molten. The BRL 39123 (penciclovir) was added to the molten oil phase and homogenised or stirred for 5 minutes. The aqueous phase was heated to 65–70° C. and stirred until complete solution was achieved. This was then added to the oil phase, kept at the same temperature and homogenised for 10 minutes. The cream was stirred while cooling and at 40–45° C., a vacuum of 0.9 bar was pulled. Stirring was continued until the cream reached a temperature of 25–30° C. Finally the cream was packed into suitable containers.

What is claimed is:

1. An oil in water or an aqueous topical pharmaceutical formulation comprising at least 30% propylene glycol and 0.5 to 10% solubilized penciclovir.

2. A pharmaceutical formulation according to claim 1 containing from 30 to 60% propylene glycol and at least 15% water.

3. A pharmaceutical formulation according to claim 2 containing from 30 to 50% propylene glycol and at least 20% water.

4. A pharmaceutical formulation according to claim 3 comprising 0.75 to 5% penciclovir, 35 to 45% propylene glycol and 25 to 40% water together with an oil phase.

5. A pharmaceutical formulation according to claim 4, comprising 1% penciclovir.

6. A pharmaceutical formulation according to claim 1 further comprising an emulsifier.

7. A method of treating a herpes viral infection in a mammal in need thereof, which method comprises topically administering to said mammal an effective amount of a pharmaceutical formulation comprising at least 30% propylene glycol and 0.5 to 10% w/w solubilized penciclovir.

8. The method according to claim 7 wherein the herpes virus is varicella-zoster virus.

9. A pharmaceutical formulation according to claim 6 wherein the emulsifier is selected from the group consisting of polyoxyethylene sorbitan monostearate (polysorbate 60), sorbitan monostearate, sorbitan monooleate, cetostearyl alcohol, myristyl alcohol, glyceryl monostearate, sodium lauryl sulphate, Cetomacrogol 1000 and Carbomer 940.

10. A pharmaceutical formulation according to claim 9 wherein the emulsifier is polyoxyethylene sorbitan monostearate (polysorbate 60).

11. A pharmaceutical formulation according to claim 9 wherein the emulsifier is sorbitan monostearate.

12. A pharmaceutical formulation according to claim 9 wherein the emulsifier is sorbitan monooleate.

13. A pharmaceutical formulation according to claim 9 wherein the emulsifier is cetostearyl alcohol.

14. A pharmaceutical formulation according to claim 9 wherein the emulsifier is myristyl alcohol.

15. A pharmaceutical formulation according to claim 9 wherein the emulsifier is glyceryl monostearate.

16. A pharmaceutical formulation according to claim 9 wherein the emulsifier is sodium lauryl sulphate.

17. A pharmaceutical formulation according to claim 9 wherein the emulsifier is Cetomacrogol 1000.

18. A pharmaceutical formulation according to claim 9 wherein the emulsifier is Carbomer 940.

19. The method according to claim 7 wherein the herpes virus is herpes simplex-1 or herpes simplex-2 virus.

20. The method according to claim 7 wherein the pharmaceutical formulation further comprises an emulsifier selected from the group consisting of polyoxyethylene sorbitan monostearate (polysorbate 60), sorbitan monostearate, sorbitan monooleate, cetostearyl alcohol, myristyl alcohol, glyceryl monostearate, sodium lauryl sulphate, Cetomacrogol 1000 and Carbomer 940.

21. The method according to claim 20 wherein the emulsifier is polyoxyethylene sorbitan monostearate (polysorbate 60).

22. The method according to claim 20 wherein the emulsifier is sorbitan monostearate.

23. The method according to claim 20 wherein the emulsifier is sorbitan monooleate.

24. The method according to claim 20 wherein the emulsifier is cetostearyl alcohol.

25. The method according to claim 20 wherein the emulsifier is myristyl alcohol.

26. The method according to claim 20 wherein the emulsifier is glyceryl monostearate.

27. The method according to claim 20 wherein the emulsifier is sodium lauryl sulphate.

28. The method according to claim 4 wherein the emulsifier is Cetomacrogol 1000.

29. The method according to claim 20 wherein the emulsifier is Carbomer 940.

* * * * *

UNITED STATES PATENT AND TRADEMARK OFFICE
CERTIFICATE OF CORRECTION

PATENT NO. : 6,469,015 B2
DATED : October 22, 2002
INVENTOR(S) : Griffiths et al.

It is certified that error appears in the above-identified patent and that said Letters Patent is hereby corrected as shown below:

Title page,
Item [30], Foreign Application Priority Data, should read:
-- Jan. 26 1990      (GB) ....................... 9001886 --.

Signed and Sealed this

Twenty-eighth Day of December, 2004

JON W. DUDAS
*Director of the United States Patent and Trademark Office*